(12) United States Patent
Stütz et al.

(10) Patent No.: US 11,835,486 B2
(45) Date of Patent: Dec. 5, 2023

(54) BIOANALYSIS TEST KIT AND METHOD FOR ANALYZING SUCH A TEST KIT

(71) Applicant: BIOMENSIO LTD, Tampere (FI)

(72) Inventors: Evamaria Stütz, Munich (DE);
Stephan Buchholz, Munich (DE);
Matthias Schreiter, Munich (DE);
Alexander Michael Gigler,
Untermeitingen (DE)

(73) Assignee: BioMensio Ltd., Tampere (FI)

( * ) Notice: Subject to any disclaimer, the term of this patent is extended or adjusted under 35 U.S.C. 154(b) by 0 days.

(21) Appl. No.: 17/955,534

(22) Filed: Sep. 28, 2022

(65) Prior Publication Data
US 2023/0019671 A1    Jan. 19, 2023

Related U.S. Application Data

(62) Division of application No. 16/090,270, filed as application No. PCT/EP2017/057171 on Mar. 27, 2017, now Pat. No. 11,493,483.

(30) Foreign Application Priority Data

Mar. 31, 2016  (DE) .......................... 102016205335.3

(51) Int. Cl.
*G01N 29/30*    (2006.01)
*G01N 29/02*    (2006.01)
(Continued)

(52) U.S. Cl.
CPC ........... *G01N 29/30* (2013.01); *G01N 29/022* (2013.01); *G01N 29/036* (2013.01);
(Continued)

(58) Field of Classification Search
CPC .... G01N 29/30; G01N 29/022; G01N 29/036; G01N 33/54373; G01N 2291/0255; G01N 2291/0256; G01N 2291/0426
See application file for complete search history.

(56) References Cited

U.S. PATENT DOCUMENTS

| | | |
|---|---|---|
| 5,932,953 A | 8/1999 | Drees et al. |
| 2007/0224700 A1 | 9/2007 | Masters |

(Continued)

FOREIGN PATENT DOCUMENTS

| | | |
|---|---|---|
| CN | 101091114 A | 12/2007 |
| CN | 101713772 A | 5/2010 |

(Continued)

OTHER PUBLICATIONS

Chinese Office Action for Chinese Application No. 201780022463.X dated Jan. 22, 2021.

(Continued)

*Primary Examiner* — Dennis White
(74) *Attorney, Agent, or Firm* — Lempia Summerfield Katz LLC

(57) ABSTRACT

A test kit that is configured for bioanalysis, such as an immunoassay, is provided. The test kit includes at least one measuring sensor for quantitative detection of a substance, and at least one reference sensor that is already supplied with the substance in a defined manner. In a method for analyzing a test kit, the at least one measuring sensor is read, and a measurement value for a concentration, a substance quantity, or a mass is obtained. A read value of the at least one measuring sensor is scaled using read values of the at least one reference sensor, or a measured value that corresponds to the read value is obtained using a compensation curve that (Continued)

puts the read values of the at least one reference sensor into relationship with the defined supply of the substance to the at least one reference sensor.

16 Claims, 2 Drawing Sheets

(51) Int. Cl.
  *G01N 33/543* (2006.01)
  *G01N 29/036* (2006.01)
(52) U.S. Cl.
  CPC .................. *G01N 33/54373* (2013.01); *G01N 2291/0255* (2013.01); *G01N 2291/0256* (2013.01); *G01N 2291/0426* (2013.01)

(56) References Cited

U.S. PATENT DOCUMENTS

| 2007/0270672 | A1 | 11/2007 | Hayter |
| 2008/0153710 | A1 | 6/2008 | Hengerer |
| 2008/0197430 | A1 | 8/2008 | Aigner |
| 2008/0220980 | A1 | 9/2008 | Lea |
| 2010/0086933 | A1 | 4/2010 | Hospach et al. |
| 2010/0227773 | A1 | 9/2010 | Abel |
| 2016/0103125 | A1 | 4/2016 | Tischer |
| 2016/0291005 | A1 | 10/2016 | Salvati et al. |

FOREIGN PATENT DOCUMENTS

| CN | 102116771 A | 7/2011 | |
| CN | 103513029 A | 1/2014 | |
| DE | 102004058064 A1 | 6/2006 | |
| DE | 102006020866 A1 | 11/2007 | |
| WO | 2015073496 A1 | 5/2015 | |
| WO | WO-2015073496 A1 * | 5/2015 | ....... G01N 33/54373 |

OTHER PUBLICATIONS

European Decision to Grant for European Application No. 17715645.2-1118/3417290 dated Nov. 5, 2020.
German Search Report for German Application No. 10 2016 205 335.3, dated Nov. 11, 2016.
PCT International Search Report and Written Opinion of International Searching Authority dated Jun. 2, 2017 corresponding to PCT International Application No. PCT/EP2017/057171 filed Mar. 27, 2017. pp. 1-13.

* cited by examiner

BIOANALYSIS TEST KIT AND METHOD FOR ANALYZING SUCH A TEST KIT

This application is a divisional patent application of U.S. patent application Ser. No. 16/090,270, filed Sep. 30, 2018, which is the National Stage of International Application No. PCT/EP2017/057171, filed Mar. 27, 2017, which claims the benefit of German Patent Application No. 10 2016 205 335.3, filed Mar. 31, 2016. The entire contents of these documents are hereby incorporated herein by reference.

BACKGROUND

The present embodiments relate to a bioanalysis test kit and a method for evaluating such test kit.

Bioanalytical tests such as pregnancy tests or addictive substances tests that use a test strip typically only supply qualitative, and not quantitative, results. For example, in the case of tests directed to end users external to a correspondingly equipped laboratory, a unique reference scale for a quantitative analysis is regularly not available.

Quantifying drugs, for example, in bodily fluids is typically also implemented at a later stage in a laboratory. For example, in the case of drugs, test kits that are already quantitatively evaluable in the field (e.g., based on saliva samples during a check) would be desirable. However, on account of the multiplicity of potentially relevant influencing parameters (e.g., quantitative measurements in the field), to the extent that these are even possible, always lag significantly behind laboratory measurements in terms of their accuracy.

Therefore, test kits that are not restricted to laboratories regularly serve, at best, as "quick preliminary tests." Typically, an analyte is applied to a test strip in the process and, for example, the occurrence of a discoloration is observed. Quantifiability is hardly possible in such test kits.

SUMMARY AND DESCRIPTION

The scope of the present invention is defined solely by the appended claims and is not affected to any degree by the statements within this summary.

The present embodiments may obviate one or more of the drawbacks or limitations in the related art. For example, an improved test kit and an improved method for acquiring bioanalytical measurement data that, for example, facilitate a reliable, quantitative test result are provided. As another example, an improved method for evaluating such a test kit and an evaluation device for evaluating such test kits are provided.

The test kit according to one or more of the present embodiments is embodied for bioanalysis (e.g., for an immunoassay). The test kit according to one or more of the present embodiments includes at least one measurement sensor for quantitative detection of a substance and at least one reference sensor, to which the substance has already been supplied in a defined manner. A defined supply of the reference sensor or sensors may be the supply with a certain concentration and/or substance amount and/or mass (e.g., absolute or relative). Accordingly, a quantitative detection may be the detection of a concentration and/or substance amount and/or mass (e.g., absolute or relative).

A reference scale is directly implemented in the test kit itself by one or more reference sensors such that the reference scale always takes account of the external influences on the test kit and hence on the measurement sensor. By way of example, temperature influences have the same effect on the reference sensor or sensors and on the measurement sensor. Further, the sensors and the substance to be measured possibly attached thereto age equally in the test kit according to one or more of the present embodiments, and so, deviations resulting therefrom act simultaneously on the measurement sensor and on the reference sensor or sensors and consequently always compensate one another.

In one embodiment, the test kit according to one or more of the present embodiments includes at least two reference sensors (e.g., at least three or more reference sensors). In one embodiment, the substance is supplied to a different extent to the reference sensors. In this way, a particularly broad reference scale for readout values of the measurement sensor may be obtained by a compensation calculation.

In a development of the test kit according to one or more of the present embodiments, the reference sensor or sensors and/or the measurement sensor or sensors is or are formed with acoustic resonators (e.g., with FBARs).

In one embodiment, sensor arrays formed with acoustic resonators (e.g., with FBARs) may detect target molecules very sensitively. FBARs are miniaturized acoustic resonators, the resonant frequency of which may be detuned in highly sensitive fashion by the attachment of molecules on the surface thereof. By way of suitable functionalizations, target molecules may be selectively bound and consequently detected in targeted manner in the process.

Any number of FBAR resonators may be integrated in a measurement sensor and/or reference sensor, with the resonators remaining individually actuatable and readable. As a result, each individual resonator represents an independent reaction surface for immunoassays, for example. For example, the resonators may be functionalized by binding antibodies or standardized antibody-antigen complexes. Further, precisely defined concentrations may easily be supplied to the resonators by compartments (e.g., on the sensor chip). Regularly and likewise particularly advantageously, acoustic resonators are formed with piezoelectric materials as known per se so that the acoustic resonators may be electrically actuated and read in a simple, automated, and reliable manner.

In one embodiment, the at least one measurement sensor and the reference sensor or sensors each include at least one acoustic resonator (e.g., an acoustic resonator that has been functionalized by antigens and/or by antibodies) in the test kit according to one or more of the present embodiments.

In one embodiment, the test kit has at least one measurement compartment per measurement sensor, the at least one measurement sensor respectively being introduced therein, and/or at least one reference compartment per reference sensor, the at least one reference sensor respectively being introduced therein. A fluid-tight separation of the measurement or reference sensors is reliably provided in this way.

In an advantageous development, the test kit according to one or more of the present embodiments is a pregnancy and/or drugs test kit. Within the scope of this application, drugs include, for example, narcotics and/or psychoactive drugs. It is impermissible to be under the influence thereof, at least above a minimum threshold, either in general or within the scope of certain activities.

In the method according to one or more of the present embodiments for acquiring measurement data for an immunoassay, use is made of a bioanalysis test kit as described above.

In the method according to one or more of the present embodiments for evaluating a test kit as described above, the measurement sensor is read and a measurement value is obtained for a concentration, a substance amount, or a mass by virtue of the readout value of the at least one measurement sensor being simply scaled using the readout values of the at least one reference sensor or a measurement value corresponding to the readout value being obtained by a compensation function or compensation curve. The compensation function or compensation curve relates the readout values of the reference sensors to the defined amounts supplied to the reference sensors.

The evaluation device according to one or more of the present embodiments is embodied to implement an evaluation method as described above. In one embodiment, the evaluation device is a constituent part of the test kit according to one or more of the present embodiments, as described above.

DETAILED DESCRIPTION

Figure 1:
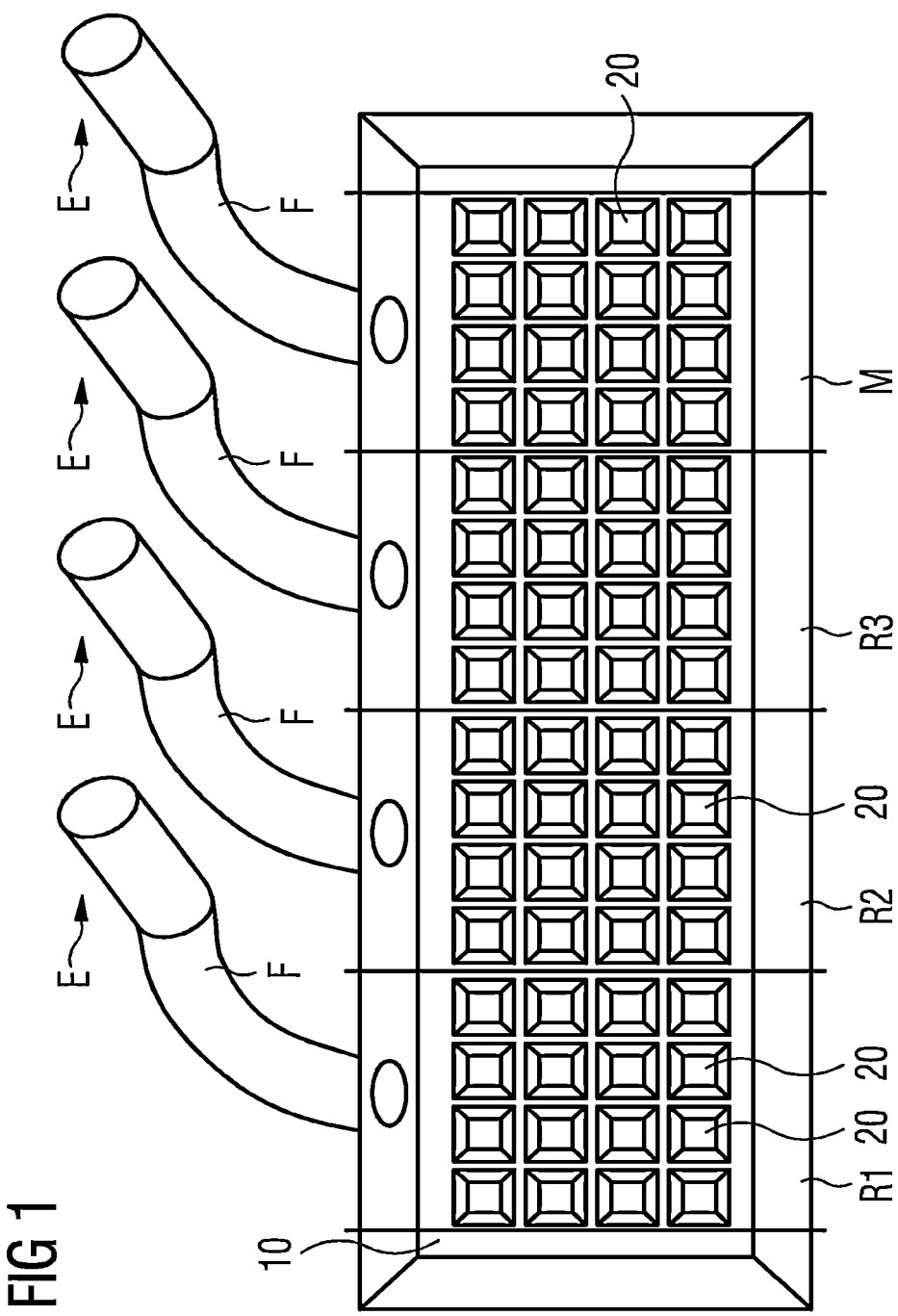
FIG. 1 schematically shows a plan view of a test kit with a compartment with a measurement sensor formed with a plurality of acoustic resonators and with three compartments with one reference sensor each, the reference sensor being formed with a plurality of acoustic resonators, during the preparation for field use.
Figure 2:
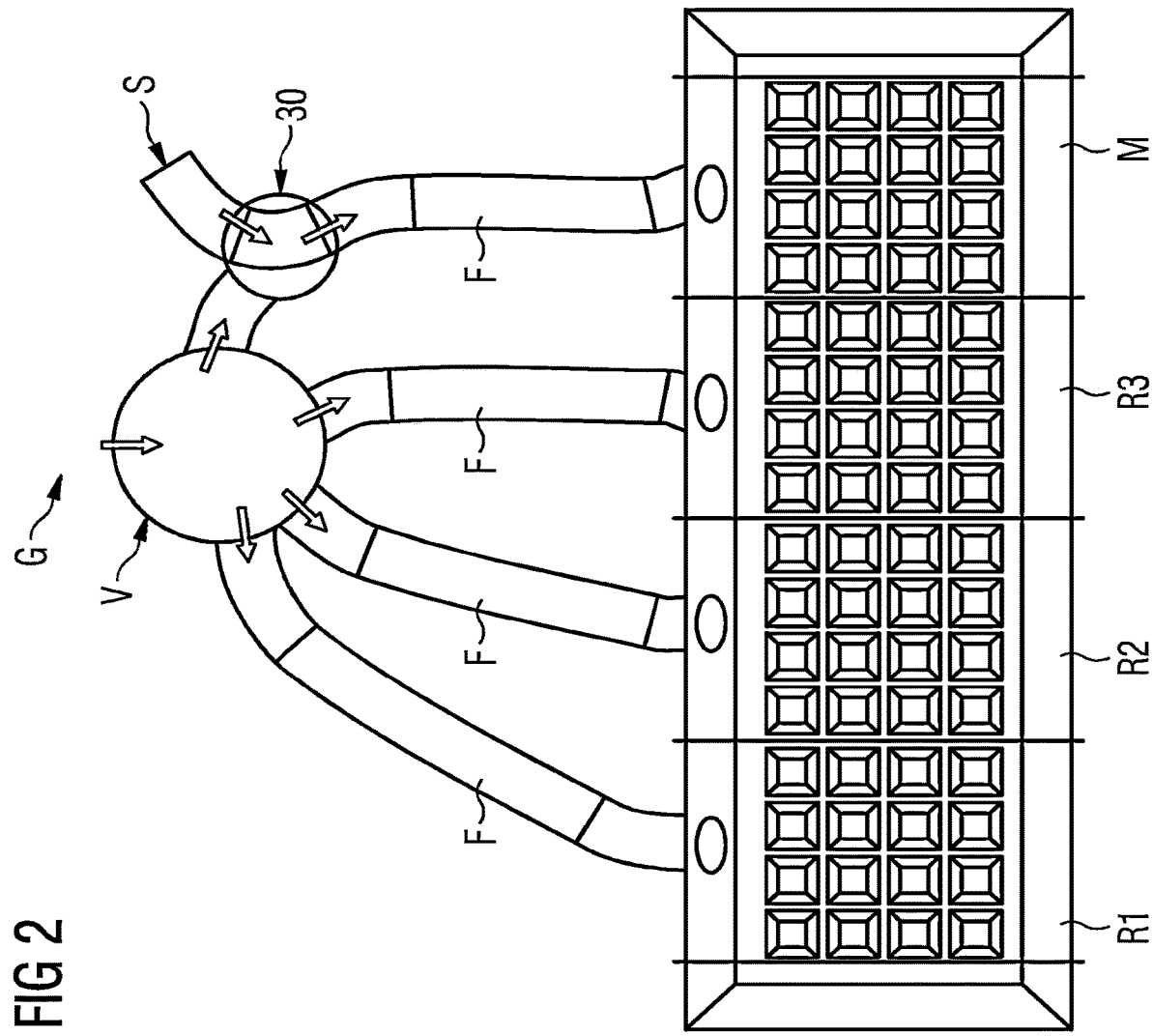
FIG. 2 schematically shows a plan view of the test kit according to FIG. 1 in the configuration during the field use.

The test kit illustrated in FIG. 1 includes a sensor chip 10 that includes an array of acoustic resonators 20 in the form of film bulk acoustic resonators (FBARs). In a manner known per se, such acoustic resonators 20 may be used to detect the attachment of substances from a detuning of the resonant frequency. In the case illustrated in FIG. 1, 16 resonators form a sensor in each case. Here, three of such sensors formed by groups of resonators respectively form a reference sensor R1, R2, R3, and a fourth group forms the actual measurement sensor M.

The reference sensors R1, R2, R3 and the measurement sensor M are separated from one another in a fluid-tight manner in each case by virtue of biocompatible compartments, formed with PBO, for example, being deposited on the chip surface by a wafer level process in a manner known per se. Each of the reference sensors R1, R2, R3 and the measurement sensor M are arranged in a single compartment in each case. A flow cell manufactured from PEEK by an injection molding is attached thereto in each case in a fluid-tight manner.

Initially, the test kit is prepared for field use as follows (e.g., by the producer after production of the test kit in the illustrated case).

Initially, the acoustic resonators 20 are functionalized. To this end, each compartment of the reference sensors R1, R2, R3 and of the measurement sensor M are attached to a fluid feed F via the respectively assigned flow cell. Initially, an assay-compatible buffer solution, a phosphate-buffered saline (PBS) in the illustrated exemplary embodiment, is supplied to each inlet E of the respective fluid feed F. Each compartment of the respective reference sensor R1, R2, R3 and of the measurement sensor M is rinsed by this buffer solution.

Subsequently, both the resonators 20 of the reference sensors R1, R2, R3 and the resonators 20 of the measurement sensor M are functionalized (e.g., coated on the surface) with a catcher antibody.

After another rinse step for each compartment of the respective reference sensor R1, R2, R3 and of the measurement sensor M, non-specific attachment surfaces of the sensor chip 10 (e.g., areas that do not form any functionalized areas of the resonators 20) are passivated. Albumin (hsa/bsa) is added in each case via the inlet E of the respective fluid supply F.

After another rinsing step for each compartment of the respective reference sensor R1, R2, R3 and of the measurement sensor M, a defined concentration of the target substance is respectively supplied to each compartment of the reference sensors R1, R2, R3 (but not to the compartment of the measurement sensor M). A different concentration of the target substance is supplied to each of the reference sensors R1, R2, R3. Subsequently, the compartments assigned to the reference sensors R1, R2, R3 and the compartment assigned to the measurement sensor M are filled with a suitable amount of preserving solution. Consequently, the sensor chip 10 may be stored until the intended field use.

In further exemplary embodiments without a dedicated illustration, additional compartments with further measurement and reference sensors are present. The additional compartments serve to measure further substances. In principle, the resonators may be functionalized by micro-spotters in further exemplary embodiments that are not presented separately below and not explained in detail here, and so, for example, individual resonators within one compartment may be functionalized for substances that differ from one another.

For field use, the feeds F with corresponding inlets E are connected to a distributor V that has a common inlet G. Further, the feed F feeding the measurement sensor is provided with a 3-way valve 30, by which either the distributor V or a sample inlet S is fluid-connectable to the compartment of the measurement sensor M. Initially, the sensor chip 10 is activated during field use by virtue of the compartments of the reference sensors R1, R2, R3 and of the measurement sensor M initially being rinsed with buffer solution. Consequently, the preserving solution is completely removed.

The measurement sensor M is fluidically decoupled by setting the 3-way valve 30, and the target substance is supplied to the measurement sensor M by the sample inlet S. The target substance is thus supplied to the measurement sensor M. The compartments assigned to the reference sensors R1, R2, R3 continue to be rinsed with the buffer solution.

Subsequently, the antigen complex fitting to the catcher antibody is supplied to all compartments of the reference sensors R1, R2, R3 and of the measurement sensor M.

Subsequently, and for the measurement, all chambers are then rinsed again with a buffer, both simultaneously and with the same flow, and the measurement of the displacement of the resonant frequency of the FBARs is carried out.

Subsequently, the measurement values of the sensor chip 10 are evaluated. The corresponding to the preceding defined supply of the reference sensors R1, R2, R3 are related to the readout values of the reference sensors R1, R2, R3. Consequently, in the illustrated exemplary embodiment, the concentrations of the target substance, supplied to the reference sensors R1, R2 and R3 when preparing the sensor chip 10, are related to the frequency shift of the resonant frequency of the acoustic resonators 20 of the respective reference sensors R1, R2 and R3. The relationship, which is linear to very good approximation, is mapped using a compensation straight line. A frequency shift of the measurement sensor M may thus be converted into concentration of the target substance using the compensation straight line.

In a further exemplary embodiment, which corresponds to the exemplary embodiment explained above, the supply of a reference sensor R1, R2, R3 is selected to have a concentration that corresponds to a limit value that is of importance, for example, for driving a vehicle, operating a machine or any other legal constraint. If the frequency shift of the measurement sensor M is compared to the frequency shift of this reference sensor, it is possible to directly deduce a concentration of the target substance above the limit value.

The details of the functionalization of the compartments may remain hidden in the exemplary embodiments explained above. Consequently, a manipulation of the sensor chip 10 is effectively prevented, or else a manipulation may easily be detected.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for acquiring measurement data for an immunoassay, the method comprising:
   acquiring the measurement data for the immunoassay using a bioanalysis test kit, the bioanalysis test kit comprising:
   at least one measurement sensor coated with an antigen, an antibody, or the antigen and the antibody, such that the at least one measurement sensor is configured to quantitatively detect a substance via binding of the substance to the antigen, the antibody, or the antigen and the antibody;
   at least one reference sensor coated with the antigen, the antibody, or the antigen and the antibody, to which a defined concentration, amount, or mass of the substance is already bound, wherein the at least one reference sensor, the at least one measurement sensor, or the at least one reference sensor and the at least one measurement sensor are formed with acoustic resonators; and
   at least one reference compartment per reference sensor, the at least one reference sensor respectively being introduced therein,
   wherein the at least one reference compartment is separated from the measurement sensor in a fluid-tight manner during measurement.

2. The method of claim 1, wherein the at least one reference sensor comprises at least two reference sensors, the substance being supplied to a different extent to each of the at least two reference sensors.

3. The method of claim 2, wherein the at least two reference sensors comprise three or more reference sensors, the substance being supplied to a different extent to each of the three or more reference sensors.

4. The method of claim 1, wherein the bioanalysis test kit further comprises:
   at least one measurement compartment per measurement sensor, the at least one measurement sensor respectively being introduced therein.

5. The method of claim 1, wherein the bioanalysis test kit is a pregnancy, drugs, or pregnancy and drugs test kit.

6. The method of claim 1, wherein the acoustic resonators are film bulk acoustic resonators.

7. The method of claim 1, wherein the at least one reference sensor is configured to implement a reference scale in the test kit.

8. The method of claim 1, wherein the at least one reference compartment is separated from the measurement sensor in a fluid-tight manner by a valve.

9. A method for evaluating a bioanalysis test kit, the method comprising:
   providing a bioanalysis test kit, the bioanalysis test kit comprising:
   at least one measurement sensor coated with an antigen, an antibody, or the antigen and the antibody, such that the at least one measurement sensor is configured to quantitatively detect a substance via binding of the substance to the antigen, the antibody, or the antigen and the antibody;
   at least one reference sensor coated with the antigen, the antibody, or the antigen and the antibody, to which a defined concentration, amount, or mass of the substance is already bound, wherein the at least one reference sensor, the at least one measurement sensor, or the at least one reference sensor and the at least one measurement sensor are formed with acoustic resonators; and
   at least one reference compartment per reference sensor, the at least one reference sensor respectively being introduced therein, wherein the at least one reference compartment is separated from the measurement sensor in a fluid-tight manner during measurement;
   obtaining a measurement value for a concentration, a substance amount, or a mass, the obtaining comprising scaling of a readout value of the at least one measurement sensor being scaled using readout values of the at least one reference sensor or a measurement value corresponding to the readout value of the at least one measurement sensor obtained by a compensation function that relates the readout values of the at least one reference sensor to the defined concentration, amount, or mass supplied to the at least one reference sensor.

10. The method of claim 9, wherein the at least one reference sensor comprises at least two reference sensors, the substance being supplied to a different extent to each of the at least two reference sensors.

11. The method of claim 10, wherein the at least two reference sensors comprise three or more reference sensors, the substance being supplied to a different extent to each of the three or more reference sensors.

12. The method of claim 9, wherein the bioanalysis test kit further comprises:
   at least one measurement compartment per measurement sensor, the at least one measurement sensor respectively being introduced therein.

13. The method of claim 9, wherein the bioanalysis test kit is a pregnancy, drugs, or pregnancy and drugs test kit.

14. The method of claim 9, wherein the acoustic resonators are film bulk acoustic resonators.

15. The method of claim 9, wherein the at least one reference sensor is configured to implement a reference scale in the test kit.

16. The method of claim 9, wherein the at least one reference compartment is separated from the measurement sensor in a fluid-tight manner by a valve.

\* \* \* \* \*